(12) United States Patent
Cegielski et al.

(10) Patent No.: US 8,278,096 B2
(45) Date of Patent: Oct. 2, 2012

(54) STEM CELL LINES FROM DEER ANTLERS, THEIR APPLICATION AND CULTURE METHODS

(75) Inventors: Marek Cegielski, Wroclaw (PL); Marek Bochnia, Wroclaw (PL); Ireneusz Calkosinski, Wroclaw (PL); Wojciech Dziewiszek, Wroclaw (PL)

(73) Assignee: Stem Cells Spin Spolka Akcyjna, Wroclaw (PL)

( * ) Notice: Subject to any disclaimer, the term of this patent is extended or adjusted under 35 U.S.C. 154(b) by 110 days.

(21) Appl. No.: 12/451,019

(22) PCT Filed: Dec. 10, 2007

(86) PCT No.: PCT/PL2007/000080
§ 371 (c)(1),
(2), (4) Date: Feb. 12, 2010

(87) PCT Pub. No.: WO2008/133536
PCT Pub. Date: Nov. 6, 2008

(65) Prior Publication Data
US 2010/0184217 A1    Jul. 22, 2010

(30) Foreign Application Priority Data

Apr. 25, 2007 (PL) .......................................... 382287
Aug. 11, 2007 (PL) .......................................... 383134

(51) Int. Cl.
*C12N 5/00* (2006.01)
*A01N 63/00* (2006.01)
*A01N 65/00* (2009.01)

(52) U.S. Cl. ..................................... 435/325; 424/93.1

(58) Field of Classification Search ............... 435/325, 435/455
See application file for complete search history.

(56) References Cited

OTHER PUBLICATIONS

Cegielski (Bulletin of the Veterinary Res. Institute in Pulawy, 2006, vol. 50, p. 247-257).*
Mount (Developmental Dynamics, 2006, vol. 235, p. 1390-1399).*
Li (J. Experimental Zoology, 2001, vol. 290, p. 18-30).*
International Search Report issued by the International Searching Authority (ISA/EP) on Feb. 16, 2009 in connection with International Application No. PCT/PL2007/000080.
Cegielski, M. et al., "Search for Stem Cells in the Growing Antler Stag (*Cervus Elaphus*)", Bull Vet Inst Pulawy, (2006) vol. 50, pp. 247-251.
Cegielski M. et al., "Experimental Application of Xenogenous Antlerogenic Cells in Replacement of Auricular Cartilage in Rabbits", Xenotransplantation (2008) vol. 15, pp. 374-383.
Li, Chunyi et al., "Tissue Interactions and Antlerogenesis: New Findings Revealed by a Xenograft Approach", Journal of Experimental Zoology (2001) vol. 290, pp. 18-30.
Mount, J.G., "Evidence That the Canonical Wnt Signalling Pathway Regulates Deer Antler Regeneration" Developmental Dynamics (2006) vol. 235, pp. 1390-1399.
Price, J., "Deer Antlers as a Model of Mammalian Regeneration" Current Topics in Developmental Biology (2005) vol. 67, pp. 1-48.

* cited by examiner

*Primary Examiner* — Michael C. Wilson
(74) *Attorney, Agent, or Firm* — Gary J. Gershik; Cooper & Dunham LLP (57) ABSTRACT

New lines of stem cells from the growing antlers of deer (Cervidae) and the application of said cells in the reconstruction of connective tissue, preferentially bone, cartilage or adipose tissue, in humans and animals; as well as a method of culturing them and the application of tissues from growing deer antlers in the production of the MIC-1 stable stem cell line.

3 Claims, 1 Drawing Sheet

STEM CELL LINES FROM DEER ANTLERS, THEIR APPLICATION AND CULTURE METHODS

The present invention relates to new stem cell lines from growing deer antlers (Cervidae) and the application of said cells in the reconstruction of connective tissue, preferentially bone, cartilage or lipid tissue in humans and animals, as well as the application of growing deer antler tissue to derive a stable stem cell line designated MIC-1. Another aspect of the present invention is a method for culturing thusly obtained cell lines.

The search for the ideal material for the reconstruction of the cartilaginous lattice of the ear lobes and nose is well over a hundred years old and are still being actively pursued. Autologous rib cartilage has been and is still being used most often as a reconstructive material in facial surgery. Unfortunately, the time required to obtain it greatly complicates the procedure, subjects the patient to greater post-surgical discomfort and increases the likelihood of subsequent complications at sampling sites. Furthermore, in children the amount of rib cartilage available for harvesting is often too small to reconstruct the ear lobe or nose, whereas in the adult it may be calcified and unusable. An important step in the search for the ideal organic reconstructive material consisted of the research of Vacanti et al. initiated during the 1990's. This pioneering research made use synthetic, biocompatible, biodegradable and porous polymer mesh which was impregnated with isolated human chondrocytes. The number of chondrocytes capable of being grown ex vivo is limited, however and it is of direct importance to the efficiency of regeneration. The technology is very expensive, tedious and requires specialized equipment. Many implants also lose their shape over time. Particular difficulties arise due to the question of species compatibility in most cases, since a strong immune reaction occurs against introduced foreign tissue, which results in implant rejection.

The onset of the XXI century is a period of very dynamic development on the use of stem cells in the regeneration and reconstruction of all manners of tissue including connective tissue. Stem cells are characterised by a large proliferation potential, both in vivo and in vitro, and the possibility of implanting them is a chance for significant progress in transplantology. In the case of most tissues, however, it is very difficult to obtain determined cell lines. Furthermore, the collection of human stem cells entails ethical problems, as well as the risk of transferring viral diseases and tumors.

The state of technology reveals solutions pertaining solely to obtaining stem cells differentiating into osteoblasts exclusively from various human tissues. Applications WO 2005/085422 and US 2005/0048644 describe stem cells isolated from lipid tissue, used in the treatment of diseases of the locomotor apparatus. Application WO 2005/038012 reveals a method of obtaining stem cells capable of differentiating into osteoblasts or chondroblasts from human foetal tissue. Application 2007/0122902 reveals a method of isolating and culturing pluripotent stem cells from placental blood. Attempts have also been made to genetically modify cells capable of regenerating cartilage and bone, as related by patent description U.S. Pat. No. 6,398,816. The largest number of ethical controversies are raised by applications relating to the isolation of stem cells from embryonic tissue (WO03068937A2, WO02064755A2, WO0038583A1).

The application of human stem cells, widely described in the state of technology, entails many problems which are evidence of the need to continue research in this respect. Some of the main problems are ethical considerations entailed by the use of embryonic tissue, the danger of genetic defects as well as the risk of transferring viral diseases and tumors. There thus exists a real and pressing need for stem cell lines, the application of which would exclude the risk of the above problems.

Each year, the mature antlers of deer (Cervidae), built of bone tissue, are jettisoned and rapidly regrown. It develops postnatally as an extension of the pedicels, which are always present on the foramen. The growth regions, stem blastema and antlers arise from a specialized area of the foramen, the so-called antlerogenic periosteum. The buds and growing antlers are constructed of a specific form of osteo-cartilage, which is a mixture of cartilage and bone. Antlers occur in all males of the 39 species in the deer family.

Antler growth in the deer, its shape and subsequent mineralization are complex and at once rapid processes. The antlers grow due to the so-called endochondral ossification process. In our climatic zone, growth is particularly rapid during a three month period, from April to June. Two-centimetre daily growth makes the growing antler one of the most rapidly growing organs in mammals. This requires the activation and collaboration of many types of cells, and stem cells play a particular role in the initiation and continuation of the process. Antlerogenic cells are of mesenchymal origin, and some of them can be considered adult somatic stem cells.

The state of technology describes the properties of deer antler tissue, recognized as the most rapidly growing form of bone among mammalian tissues. Attempts have been made to utilize the growth properties of this tissue, primarily through the isolation of growth factors. Application WO 93/19085 reveals a method of isolating a growth factor, as a substance capable of regenerating damaged bone tissue. The authors revealed a method of obtaining an extract isolated from the antlers of the Sika deer (*Cervus nippon*), which stimulates the growth of haematopoietic stem cells and megakaryocytes. Application WO 2004/112806 reveals a composition for the treatment of neuronal dysfunctions, based on growth factor markers obtained from deer antlers. To date, however, it has proved impossible to obtain a stable stem cell line from deer antlers, which could successfully be used in the reconstruction of connective tissue lesions, nor a method for culturing thereof.

The goal of the present invention is to obtain stable lines of stem cells for the reconstruction of connective tissue, preferentially cartilage, bone or fatty tissues, both human and animal. Furthermore, a goal of the present invention are stem cell lines which poorly induce immune responses, which will enable them to be used in xenogenic implants, meaning cross-species. A particular goal of the present invention is the obtainment of a method of culturing this type of cell. A goal of the present invention is also the obtainment of such stem cell lines, whose application would bypass ethical considerations, the danger of genetic defect formation, as well as risks of viral disease and tumour transfer.

Unexpectedly, the above stated goal has been achieved in the present invention. The subject of the present invention is the application of tissues from growing deer antlers, preferentially from the tips of the lateral outgrowths of the growing antler, to obtain a stem cell line. In turn, another subject of the present invention is the application of the stem cell line obtained in the production of preparations to be used as cross-species implants. Another subject of the present invention is the application of the stem cell line obtained in the production of preparations for the reconstruction of connective tissue lesions, preferentially bone, cartilage or adipose tissue. The next subject of the present invention is a new stem cell line designated MIC-1 derived from the growing antlers of deer (Cervidae), deposited at the DSMZ bank under accession number DSM ACC2854. The next subject of the present invention is the application of MIC-1 cells in the reconstruction of connective tissue lesions, preferentially bone, cartilage or adipose tissue.

The present invention also relates to a method of culturing stem cells derived from growing deer antlers, particularly the European deer, based on a primary culture, directly therefrom or from previously frozen cells.

The crux of this aspect of the present invention rests on the fact that the primary culture is established from deer antler fragments collected under sterile conditions, which are homogenized, the cells are then isolated and cultured using MEM as a growth medium containing 10% foetal calf serum, glutamine and selected antibiotics, maintained in an atmosphere of 5% $CO_2$ at 37° C. After the fifth passage, the cells are frozen or maintained in the above conditions, on identical medium, where after the correct number of cells is established (at least $2 \times 10^6$) they are trypsinated in a solution of trypsin and 0.02% ethylenediaminotetraacetic acid (EDTA) and centrifuged in complete culture medium. The precipitate is suspended in fresh MEM and lattice fragments are produced, using fibrin sponges cut to a size required for lesion replacement. It is placed in sterile vials and the cell suspension is added (at least $2 \times 10^6$ cells/1 ml liquid). The cells are settled onto the lattice through centrifugation, and the supernatant is removed.

Unexpectedly, it turned out that xenogenic cells could be an alternative to human stem cells. While searching for sources of such cells, attention was turned towards deer antlers, characterized by their peculiar growth and renewal process, unparalleled anywhere else. Research results show that amongst the cells participating in annual antler renewal, there is a pool of cells endowed with a high proliferation potential. These form a limited array of differentiated cells which participate in, amongst other processes, the regeneration of damaged cartilage, bone and adipose tissue. Since antlerogenic cells are poorly differentiated, inducing a low level of immune response, it turned out that the chances of accepting xenogenic, cross-species, implants composed of said cells is very high. The analysis performed and stem cell research lead to the conclusion that there is an urgent need to establish stable stem cell lines. Unexpectedly, it turned out that antlerogenic cells induce a weak immune response due to their low level of differentiation, thanks to which they are very useful in the implantation and acceptance of xenogenic implants, both in animals and in the human. It was shown that tissues originating from the tips of the lateral protrusions of growing antlers of deer (Cervidae) can be a valuable source of a stable line of stem cells. Research performed by the Inventors shows that a number of these cells from the antlerogenic periosteum gradually change their location upwards during the growth process.

Figure 1A:
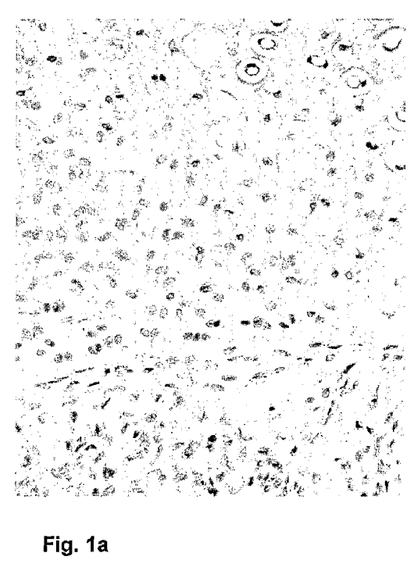
FIG. 1*a* and FIG. 1*b* present haematoxylin and eosin (H+E) staining (×200) of antlerogenic cells following implantation within the cartilage in a rabbit ear. These cells are repairing a lesion in the cartilage.
Figure 1B:
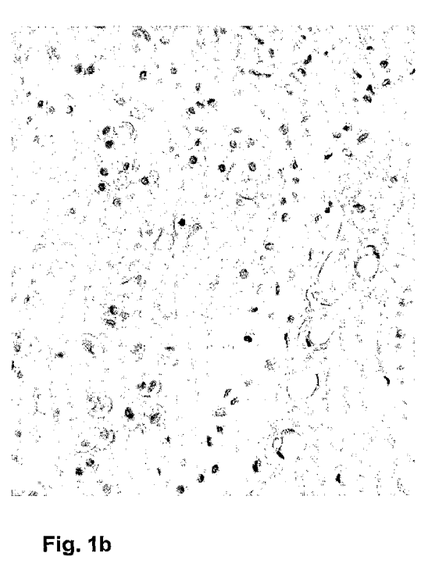

FIG. 1 shows two microscope slides (FIG. 1A and FIG. 1B) illustrating an aspect of the present invention of antlerogenic cells following implantation within the cartilage in a rabbit ear. The antlerogenic cells are visualized using haematoxylin and eosin (H+E) staining (×200). In both FIG. 1A and FIG. 1B, these cells are repairing a lesion in the cartilage.

The subject of the present invention is presented in graphic form, in which.

The present description has been supplemented by examples of embodiments of the present invention being claimed. They are solely meant to better illustrate the nature of the present solution, and should not be limiting to the scope of protection requested.

EXAMPLE 1

Isolation of a Stem Cell Line from Deer Antlers and its Application

Unexpectedly, it was shown that excisions of tissue from growing deer antlers, preferentially from the tips of the lateral protrusions of the growing deer (Cervidae) antlers may constitute a valuable source of a stable stem cell line, since, as the Inventors' research shows, that along with antler growth, their location moves slowly upward from the antlerogenic periosteum. For the above reasons, in order to obtain a new stem cell line, circular fragments of the apical lateral protrusions of growing deer (Cervidae) antlers 1.5 cm by 0.2 mm are collected under sterile conditions and shallow, remotely injected anaesthesia (often used in animal therapy). Using light microscopy it was determined that the central portion of the sections are occupied by blood vessels, in the vicinity of which are numerous, small, densely packed cells. Peripherally, the number of these cells increases considerably. A portion of the cells is larger and more mature morphologically and is reminiscent of cartilage cells (chondroblasts, chondrocytes). In between these cells there is a matrix with a growing number of collagen fibers. The external layer of the growing antler is an innervated, vascularized haired skin, the so-called velvet. Following the removal of this layer, the sections are mechanically degraded until microscopic fragments are obtained, hundreds of micrometers across. Proliferating cells are isolated using migration. A primary culture is established from the isolated cells, using a culture medium with an addition of 10% foetal calf serum as well as a solution penicillin and streptomycin. The liquid occupies at least 20% of the volume of the growth chamber. The culture is maintained under standard conditions in an atmosphere containing 5% $CO_2$ at 37° C., through at least three passages. The derived cell line is frozen and maintained in liquid nitrogen in standard cryo containers. When it becomes necessary to proliferate the line, it is unfrozen and further cultured in an identical manner, over a period necessary to generate a sufficient number of stem cells.

The presence of stem cells is confirmed by the virtual immortality of cultured cells, the absence of differentiating morphological characteristics and positive immunocytochemical results.

Ultrastructural studies were performed using electron microscopy on cells from the antler sections as well as cultured cells. The ultrastructure of small, oval, undifferentiated cells was examined in particular. It was determined that in both cases, they are characterized by a large cell nucleus, containing active, loosely packed chromatin and a nucleolus. A small amount of cytoplasm surrounds the nucleus and contains an extensive rough endoplasmic reticulum, mitochondria, vacuoles and glycogen grains. Microvilli are observed on the surfaces. This research showed that among cultured cells, there are always small, non-adherent undifferentiated, oval, opalizing cells with an extensive proliferation potential. These cells are characterised by a high survival rate, activity following freezing in liquid nitrogen and thawing. They re-establish their life functions.

Immunocytochemical reactions performed on histological samples showed a large number of proliferating cells, expressing the antigens Ki-67 and PCNA. The tagged cells are found in the proximity and within the blood vessels located centrally in the growing antler. A fair number of these, with a decidedly more zone-oriented localization, are located more peripherally and are found immediately underneath the exocrine portions of skin glands. Tagged cells are observed both within the glands themselves and in the proliferative layer of the epithelium. The reactions for the presence of vascular proliferation markers, CD31 and CD34 were negative. Positive identification using anti-Bcrp1 and anti-c-kit antibodies, denoting stem cells, was obtained in the intensive cell division zone between the skin and its immediately adjacent perichondrium.

Examination of the derived stem cell line after several days of observing the stem cell line culture under a reverse phase contrast microscope showed that spontaneous divisions were occurring as was cell differentiation. Similar results were obtained using microculture slides stained using H+E.

The culture always possessed small, non-adhering, oval, opalescent cells. Over time these become larger and grow peripheral protrusions, using which they often adhere to each other or to the substrate. Cell growth is unlimited, and after many passages they retain the ability to divide.

Research on the application of stem cells obtained from deer antlers was performed to answer the question whether cultured xenogenic cells will survive and undertake their life functions within alien tissue. To establish this, an attempt was made to use a xenogenic implant of stem cells from a growing deer antler to regenerate a lesion in the ear cartilage of a rabbit.

The primary culture is established from growing deer antler fragments collected under sterile conditions, which are degraded, cells are isolated and cultured using MEM culture medium with 10% foetal calf serum and a solution of glutamine and selected antibiotics, maintained in an atmosphere containing 5% $CO_2$ at 37° C. Following the fifth passage, the cells are frozen, or the culture is maintained under the above conditions, in an identical medium. Following the appearance of an appropriate number of cells (at least $2 \times 10^6$) they are detached using trypsin in 0.02% EDTA and centrifuged in the whole medium. The precipitate is suspended in fresh MEM and lattice fragments are produced, using fibrin sponges cut to a size required for lesion replacement. It is placed in sterile vials and the cell suspension is added (at least $2 \times 10^6$ cells/1 ml liquid). The cells are settled onto the lattice through centrifugation, and the supernatant is removed. The implants consisted of cultured cells obtained in accordance to the present invention, on a lattice, which was a fibrin sponge. Healing was observed during the clinical observation performed simultaneously following experimental (group E) and control (group C) implantation. All animals taking part in the trial bore the surgery well. Post-surgical wounds underwent rapid, proper healing. The sutures were removed 8 days following surgery. At the sites of intraperichondrial implants consisting of stem cells suspended on the fibrin sponge, the stem cells participated in the regenerative process, without immune titres nor implant rejection. The intense regenerative process resulted in a noticeable increase in cartilage thickness over the initial 3 weeks of the experiment. This process was then gradually slowed down. During week 7 of the experiment, the newly formed ear lobe structural cartilage was covered with unaltered skin, slightly uneven, and about 15% thicker than the surrounding cartilage. Additional growth in thickness of the ear lobe was not observed over the next 2 weeks. The fibrin sponge soaked in physiological saline implanted in control rabbits underwent degradation without necrosis or immune titres, but the areas where it had been implanted remained convex. After 9 weeks, these spots were still considerably thinner, and covered on both sides by unaltered skin. No regenerative processes were observed here, only scarring.

During week 4, around the periphery of the regenerating area, one observes a large number of proliferating, undifferentiated cells arrayed in bands. In certain areas small blood vessels appear between them. In the center of the implant, the layout of the cells becomes sparser, and collagen fibers appear between them. Initially, they have a regular, band-wise layout, and subsequently their layout becomes chaotic with frequent interweaving. Numerous fibroblasts and fibrocytes become localized between the collagen fibers, and less frequently chondrocytes, as well as local accumulations of lymphocytes and eosinophyllic granulocytes. The center of the regeneration zone is occupied by a basal matrix which undergoes organization and restructuring by numerous connective tissue cells such as fibroblasts, chondroblasts, osteoblasts as well as numerous structures of a condensed matrix. Morphologically, these structures are similar to osteo-cartilaginous and bony bars, which contain pores with active osteoclasts. Following 9 weeks, a decreased number of cells is observed along with an increase in the number of collagen fibers. Numerous calcifications and single ossification centres are observed in the more mineralized basal matrix.

The immunocytochemical research performed made it possible to localise cells expressing the proteins in Thy-1 and CX-CR4, characteristic of stem cells, within the implant. The tagged cells were found adjacent to and within blood vessels as well as in the zone of intensively proliferating, undifferentiated cells at the border between the implant and ear lobe cartilage, as well as at the reconstruction zones of the osteo-cartilaginous bars.

Electron microscopy enables us to make the following conclusions:

In a majority of the electron microscopy images of regenerating zones at both 4 and 9 weeks relatively numerous cells are observed along with a large number of collagen fibers. After 3 weeks of regeneration, their cytoplasm contains extensive rough ER with frequently distended cisterns, numerous mitochondria with a homogenous matrix and poorly delineated cristae, as well as numerous vacuoles. Nuclei in these cells contain large amounts of loosely knit chromatin. Small, membrane-bound fragments of cytoplasm are also observed, which detach from cells and become a part of the extracellular matrix and participate in its mineralization. During week 9 of the experiment the number of cells is smaller, but the amount of collagen grows. In many cells both the cell membrane and the nuclear envelope exhibit invaginations, and the chromatin becomes condensed. Numerous cells undergo apoptosis, and exhibit nuclei typical of apoptotic cells, in which the chromatin is condensed and their cytoplasm becomes fragmented. After 3 weeks, the cartilage growth slowed markedly, whereas after 9 weeks the lesion in the cartilaginous structure in the ear lobe was completely repaired. Electron microscopy showed numerous apoptotic cells here. Apoptosis is responsible for the morphogenesis of growing antlers and also is a mechanism which exerts a regulatory effect on regeneration, limiting among others excessive cell growth. Similar regulatory processes occur during skeletal development, during bone growth and restructuring.

Using electrophoresis, the sera of experimental and control animals were fractionated into proteins such as albumins, globulins $\alpha_1, \alpha_2, \beta_1, \beta_2$ and gammaglobulins. Individual fractions were quantified in absolute and relative units, and the ratio of albumins to globulins was calculated. The electrophoretic separation of serum proteins demonstrates the behaviour of a wide spectrum of fractions, which includes acute phase proteins and immunoglobulins. Albumins are the negatively reacting fraction, whereas the proteins contained in the $\alpha_1$, $\alpha_2$, $\beta_1$, $\beta_2$ globulin fractions react positively to different degrees and at varying rates. The role of the pots-surgical trauma and disruption of tissue integrity as inducers of acute phase response can be reasonably disregarded, since all animals from both groups underwent identical procedures. When comparing the protein patterns of the experimental and control groups of animals implanted with antlerogenic cells, we only observed a small increase in the $\beta_2$ globulin fraction, on the borderline of statistical significance. This was correlated with the simultaneously observed low inflammation level against xenogenic cells. Limited angiogenesis and massive collagen synthesis, accompanied by a lack of neutrophil infiltration which would activate proteolysis are evidence of the regenerative activity of antlerogenic cells. The immune response of post-surgical animals was by the same token very weak and not accompanied by implant rejection.

The table below presents the electrophoretic separation of rabbit serum proteins from the experimental and control groups.

|  |  |  | Group C N 6 | Group E N 6 |
|---|---|---|---|---|
| Total protein |  | g/l | 60.9 ± 14.7 | 57.4 ± 11.3 |
| Albumins |  | g/l | 41.7 ± 3.6 | 37.6 ± 7.2 |
|  |  | % | 67.2 ± 4.83 | 65.8 ± 4.68 |
| Globulins | Alfa 1 | g/l | 2.8 ± 1.6 | 1.7 ± 0.8 |
|  |  | % | 4.22 ± 2.05 | 2.98 ± 1.27 |
|  | Alfa 2 | g/l | 3.8 ± 1.2 | 2.6 ± 0.7 |
|  |  | % | 5.95 ± 1.36 | 5.28 ± 1.06 |
|  | Beta 1 | g/l | 5.3 ± 1.4 | 4.9 ± 1.7 |
|  |  | % | 8.57 ± 2.07 | 11.01 ± 4.6 |
|  | Beta 2 | g/l | 2.03 ± 0.75 | 2.4 ± 0.62 |
|  |  | % | 3.37 ± 1.26 | 4.18 ± 1.16 |
|  | Gamma | g/l | 6.35 ± 1.73 | 7.03 ± 1.89 |
|  |  | % | 10.38 ± 2.83 | 12.42 ± 2.79 |
| Albumins/Globulins |  |  | 2.04 ± 0.61 | 1.97 ± 0.42 |

The antlerogenic cells obtained according to the present invention were not rejected by a representative group of animals of a different species (rabbits). To the contrary, they took part in the regeneration of cartilage along with the host tissues which tolerated their presence. This facilitates the speculation that there are realistic chances of using stem cells obtained in this manner in humans as well. Cell implants according to the present invention make it possible to avoid a series of difficulties in the regeneration of connective tissue in humans met when using standard methods, which bear the risk of transferring viral or genetic diseases or tumors. Ethical considerations connected with obtaining human stem cells for this purpose are also avoided. The successful attempt at the implantation of antlerogenic cells indicates that due to the limited expression of histocompatibility antigens, there is a large likelihood of using xenogenic stem cells in regenerative medicine. Thus, antlerogenic cells may, in the future, find use in the reconstruction of connective tissue.

EXAMPLE 2

Establishment of the MIC-1 Stem Cell Line and its Characteristics

Circular excisions 1.5 cm by 0.2 mm were collected from the tip lateral fragments of the growing antlers of *Cervus elaphus*, during the period of most intensive growth (May), under sterile conditions, under narcosis via remote injection. The excisions collected were mechanically degraded until microscopic fragments from 100 to 900 micrometers were obtained. One half of the degraded tissue was retained for light and electron microscope analysis. Proliferating cells were isolated from the portion of the degraded antler using cell migration. Isolated cells were placed in culture flasks. The medium used was SmGM-2 SingleQuots from CAMBREX, with L-glutamine at 1 mM/ml, Penicillin at 100 U/ml, and Streptomycin at 0.1 mg/ml (SIGMA, Germany). The cells were placed in an incubator, where they were grown at standard conditions in an atmosphere containing 5% $CO_2$ at +37° C. The line was maintained for four months, at an efficiency of about 5 million cells per week. The derived MIC-1 cell line was frozen and placed in cryo containers in liquid nitrogen at 176° C.

Subsequently, comparative and ID examinations were performed. Samples for microscopic analysis were fixed in 4% buffered formalin, dehydrated and embedded in paraffin blocks. Microscope slides were H+E stained.

Immunocytochemical analyses were performed using the following antibodies: anti-Ki-67 and anti-PcNA (proliferation markers), anti-CD-31 and anti-CD-34 (blood vessel markers) and anti-CX-CR4, anti-c-kit, anti-Thy-1 and anti-Bcrp-1 (stem cell markers).

Material for electron microscopy was fixed in 2.5% glutaryaldehyde in cacodylate buffer (0.1 M) pH 7.4, and then dehydrated and embedded in Epon 812 resin. The sections were contrasted using a routine method and observed on a JEM-100 B electron microscope.

Immunocytochemical reactions were performed on microculture preparations, in an attempt to identify stem cells using specific markers: anti-CXCR4, anti c-kit, anti-Thy-1 and anti-Bcrp-1. A specific, positive membrane reaction was obtained only in the case of the small, oval, frequently dividing cells using the anti-c-kit and anti-Thy-1 antibodies. We did not observe the expression of the antigens Bcrp-1 and CXCR4. The expression of the above-mentioned antigens was not observed in more differentiated cells possessing cytoplasm tic protrusions. Positive immunocytochemical results were also obtained on paraffin sections, using specific antibodies against stem cells with antibodies against anti-Bcrp1 and anti-c-kit.

Electron microscopy was used to study the ultrastructure of both culture cells and those from antler sections. We primarily examined the ultrastructure of small, oval, undifferentiated cells. In both cases, they are characterized by a large cell nucleus possessing loose chromatin and a nucleolus. A small volume of cytoplasm surrounds the nucleus and contains an extensive rough ER, mitochondria, vacuoles and glycogen grains. Microvilli are observed on the cell membrane.

Genotyping of the MIC-1 Stem Cell Line

The genotype of the MIC-1 stem cell line from the deer *Cervus elaphus* was determined on the basis of 11 polymorphic two- and four-nucleotide microsatellites. For comparison, sika deer (*Corvus nippon hortulorum*) DNA was used.

The PCR reaction mix was prepared using the QIAGEN Multiplex PCR Kit (Qiagen) and appropriate primer pairs forward and reverse. The forward primers were 5' end tagged with the fluorochromes FAM, HEX or TET, and following synthesis purified using HPLC. PCR was performed in a GeneAmp PCR System 9700 (Applied Biosystems) thermocycler, under the following conditions:

| | |
|---|---|
| initial denaturation: 95° C., 15 min. | |
| denaturation: 94° C., 30 sec. | |
| annealing: 57° C., 90 sec. | 32 cykle |
| elongation: 72° C., 60 sec. | |
| final elongation: 72° C., 10 min. | |

Genotyping was performed using capillary electrophoresis on an ABIPrism 310 (Applied Biosystems) system.

GENOTYPE of the MIC-1 stem cell line

| No. | Polymorphic marker | GenBank accession | MIC-1 cell genotype | Sika deer genotype |
|---|---|---|---|---|
| 1 | T108 | AF191798 | 147 bp | 143/155 bp |
| 2 | T156 | AF192396 | 130/158 bp | 158/166 bp |
| 3 | T193 | AF192398 | 189 bp | 221/237 bp |
| 4 | T501 | AF442815 | 244/256 bp | 252/256 bp |
| 5 | T115 | AF193021 | 168/204 bp | 180 bp |
| 6 | T107 | AF193019 | 243/247 bp | 243 bp |
| 7 | T172 | AF192397 | 161/165 bp | 173/185 bp |
| 8 | T507 | AF442816 | 199/203 bp | 139 bp |
| 9 | Haut14 | AF236378 | 106/132 bp | 120/148 bp |
| 10 | CSSM19 | AF232761 | 141/145 bp | 147/155 bp |
| 11 | CSSM66 | AF232764 | 165/179 bp | 175/189 bp | bp—base pairs.

Primer sequences

| No. | Primer name | | Sequence |
|---|---|---|---|
| 1 | T108 | forward | 5'-CATGTGGAGATAGGTAGACAGA-3' |
| | | reverse | 5'-CCATTCTGAGTAGCTGATTCA-3' |
| 2 | T156 | forward | 5'-TCTTCCTGACCTGTGTCTTG-3' |
| | | reverse | 5'-GATGAATACCCAGTCTTGTCTG-3' |
| 3 | T193 | forward | 5'-AGTCCAAGCCTGCTAAATAA-3' |
| | | reverse | 5'-CTGCTGTTGTCATCATTACC-3' |
| 4 | T501 | forward | 5'-CTCCTCATTATTACCCTGTGAA-3' |
| | | reverse | 5'-ACATGCTTTGACCAAGACC-3 |
| 5 | T115 | forward | 5'-AATGTCTGACTCTAGGTGAGTG-3' |
| | | reverse | 5'-TTTGCTATCTGACCACTAG-3' |
| 6 | T107 | forward | 5'-ACATCCGTTCAGGTGTGA-3' |
| | | reverse | 5'-CCAGAGGTAAGATAAATGGTGA-3' |
| 7 | T172 | forward | 5'-AGCATCTCCCCTTTCAACA-3' |
| | | reverse | 5'-CTTCCCAACCCAAGTATCG-3' |
| 8 | T507 | forward | 5'-AGGCAGATGCTTCACCATC-3' |
| | | reverse | 5'-TGTGGAGCACCTCACACAT-3' |
| 9 | Haut14 | forward | 5'-CCAGGGAAGATGAAGTGACC-3' |
| | | reverse | 5'-TGACCTTCACTCATGTTATTAA-3' |
| 10 | CSSM19 | forward | 5'-TTGTCAGCAACTTCTTGTATCTTT-3' |
| | | reverse | 5'-TGTTTTAAGCCACCCAATTATTTG-3' |
| 11 | CSSM66 | forward | 5'-AATTTAATGCACTGAGGAGCTTGG-3' |
| | | reverse | 5'-ACACAAATCCTTTCTGCCAGCTTGA-3' |

The MIC-1 stem cell line was deposited on Jul. 26, 2007 in the DSMZ—Deutsche Sammlung von Mikroorganismen and Zellkulturen GmbH in Braunschweig, an institution with the status of a international deposit agency for patent protection (IDA). The patent deposit was assigned the number DSM ACC2854.

EXAMPLE 3

Application of the MIC-1 Cell Line in Xenogenic Implants

A circular fragment of a growing antler 1.5 cm by 0.2 mm is collected under sterile conditions from an animal under narcosis. The collected tissue fragment is divided into four parts. The part destined for the cell culture is placed in a test tube, submersed in 10 ml of culture medium—MEM from Cambrex with the addition of penicillin 100 U.I./ml and streptomycin 0.1 mg/ml. Under laboratory conditions, the section is washed several times in the medium containing said antibiotics. Next, it is mechanically degraded into small fragments several hundred micrometers across. Proliferating cells are isolated from this material using their spontaneous migration. Following isolation, the cells are suspended in full culture medium, in a volume at least 20% of the culture chamber, with 10% foetal calf serum, 100 U.I./ml penicillin, 0.1 mg/ml streptomycin, 1 mM/ml L-Glutamine. They are then transferred into 25 cm$^2$ culture bottles. The culture is maintained in a Kendro incubator under standard conditions, meaning +37° C., in 5% $CO_2$. After a complete monolayer was obtained, the cells are detached from the culture flasks using 0.05% trypsin with 0.02% EDTA and are transferred into successive culture flasks. A continuous line is derived from such a primary line, and after the fifth passage the cells are frozen with the addition of 10% dimetylosulfoxide (DMSO) and are stored in liquid nitrogen at −176° C. In order to prepare cells for implantation, the fifth passage is unfrozen and the cells are further cultured in an identical full medium. After an appropriate number of cells are produced ($5 \times 10^6$) they are detached from the substrate using trypsin and EDTA, and then centrifuged in the medium. The serum within the medium inactivates the trypsin and the precipitate produced is suspended in fresh MEM without serum, L-glutamine nor antibiotics. The cells are counted in a Barker chamber and a suspension of $2 \times 10^6$ cells per implant are sampled for settlement on the lattice. Fibrin sponge fragments are used for this purpose, which are also used in surgery for haemostasis, here as a carrier for adherent cells. The sponge is placed in a sterile plastic vial and the suspension containing $2 \times 10^6$ cells/1 ml of clean MEM are added. This is then centrifuged, and the cells settle onto the sponge. The centrifugation was performed on a Hereus centrifuge for 10 minutes at about 700 rpm. The supernatant is decanted, leaving ready to implant cells on the fibrin sponge. For the implantation, we used cells from a culture carried out as above, on a lattice for implantation, which was a fibrin sponge.

The experiment made use of 12 rabbits, 6 in the experimental group (E) and 6 as the control group (C). These were eight-month-old white California rabbits weighing 3.5-4.0 kg. In the middle of the ear lobe, on its outer side we carried out a standard surgical prep. The skin surface was shaved, cleaned and disinfected. App. 1 cm from the edge of the lobe, we excised a flap of skin and perichondrium 1×1 cm. We then excised and removed a fragment of the bared cartilage 0.8× 0.8 cm. Small, bleeding vessels were stoppered using electrocoagulation. In the 6 E rabbits, the cartilage lesion was filled with a piece of cut-to-size fibrin sponge saturated with the cell suspension, always on the right side. An identical procedure was carried out fir the 6 C rabbits, which were implanted with a fibrin sponge saturated with physiological saline. The implants were then covered with the skin-perichondrium flaps. The wounds were closed with single-layered suture. They were then washed with hydrogen peroxide and left uncovered, without bandaging. The surgery was performed under an antibiotic screen, with 50 000 U.I./kg of penicillin administered intramuscularly. Using clinical observation, experimental material was collected ex vivo from the implant sites in both groups of animals, 4 and 9 weeks following surgery. The material was collected in the form of excisions through the whole thickness of the ear lobe, containing both the implant and the animal's own cartilage. The material obtained was fixed for immunocytochemical examination and electron microscopy.

For immunocytochemistry, the material was fixed in 4% buffered formalin, dehydrated and embedded in paraffin. Light microscopy sections were stained with H+E and toluidine, T. Paraffin sections were used for immunocytochemistry using the anti-CX-CR4, anti-c-kit and anti-Thy-1 antibodies, which recognize proteins specific for stem cells.

Material for electron microscopy was fixed in 2.5% glutarylaldehyde in cacodylate buffer (0.1 M, pH 7.4), and then dehydrated and embedded in Epon 812 resin. Electrophoresis of serum proteins was performed 4 weeks following surgery, on 2 ml samples of blood collected from the lateral ear vein. The blood was incubated in a standard fashion at 37° C. for 0.5 hours, and then centrifuged for 5 minutes to separate the serum. The separation was performed on a buffered agarose gel, using high-voltage horizontal electrophoresis. Quantification was performed using a densitometer set at 600 nm, obtaining individual protein fractions. The albumin to globulin ratio was also determined. The results obtained from the electrophoresis underwent statistical analysis using Student's t-test, at an a level of 0.05. The test was performed using Statistica 7.0 (Stat Soft).

The electrophoretic separation of the sera of both control and experimental animals yielded fractions of proteins such as albumins, globulins $\alpha_1$, $\alpha_2$, $\beta_1$, $\beta_2$ and gammaglobulins. Individual fractions were quantified in absolute and relative values, and the ratio of albumins to globulins was calculated. Electrophoresis shows the behaviour of a wide spectrum of fractions, which include acute phase proteins and immunoglobulins. Albumins are in this case the negatively responding fraction, whereas proteins in the $\alpha_1$, $\alpha_2$, $\beta_1$, and $\beta_2$ globulin fractions react positively to different degrees and at varying rates. The role of the post-surgical trauma and disruption of tissue integrity as inducers of acute phase response can be reasonably disregarded, since all animals from both groups underwent identical procedures. When comparing the protein patterns of the experimental and control groups of animals implanted with antlerogenic cells, we only observed a small increase in the $\beta_2$ globulin fraction, on the borderline of statistical significance. This was correlated with the simultaneously observed low inflammation level against xenogenic cells. Limited angiogenesis and massive collagen synthesis, accompanied by a lack of neutrophil infiltration which would activate proteolysis are evidence of the regenerative activity of antlerogenic cells. The immune response of post-surgical animals was by the same token very weak and not accompanied by implant rejection.

The table below presents the electrophoretic separation of rabbit blood serum proteins from both the experimental and control groups.

|  |  |  | Group E N 6 | Group C N 6 |
|---|---|---|---|---|
| Total protein |  | g/l | 57.4 ± 11.3 | 60.9 ± 14.7 |
| Albumins |  | g/l | 37.6 ± 7.2 | 41.7 ± 3.6 |
|  |  | % | 65.8 ± 4.68 | 67.2 ± 4.83 |
| Globulins | Alfa 1 | g/l | 1.7 ± 0.8 | 2.8 ± 1.6 |
|  |  | % | 2.98 ± 1.27 | 4.22 ± 2.05 |
|  | Alfa 2 | g/l | 2.6 ± 0.7 | 3.8 ± 1.2 |
|  |  | % | 5.28 ± 1.06 | 5.95 ± 1.36 |
|  | Beta 1 | g/l | 4.9 ± 1.7 | 5.3 ± 1.4 |
|  |  | % | 11.01 ± 4.6 | 8.57 ± 2.07 |
|  | Beta 2 | g/l | 2.4 ± 0.62 | 2.03 ± 0.75 |
|  |  | % | 4.18 ± 1.16 | 3.37 ± 1.26 |
|  | Gamma | g/l | 7.03 ± 1.89 | 6.35 ± 1.73 |
|  |  | % | 12.42 ± 2.79 | 10.38 ± 2.83 |
| Albumins/Globulins |  |  | 1.97 ± 0.42 | 2.04 ± 0.61 |

The invention claimed is:

1. A line of stem cells designated MIC-1 derived from the growing antlers of deer (Cervidae) deposited at DSMZ under accession DSM ACC2854.

2. An implant comprising stem cells on a fibrin sponge lattice, wherein the stem cells are the line of stem cells according to claim 1.

3. A process of preparing an implant comprising:
a) obtaining the stem cells of claim 1; and
b) contacting the stem cells with a fibrin sponge lattice.

* * * * *

SEQUENCE LISTING

<160> NUMBER OF SEQ ID NOS: 22

<210> SEQ ID NO 1
<211> LENGTH: 22
<212> TYPE: DNA
<213> ORGANISM: artificial
<220> FEATURE:
<223> OTHER INFORMATION: primer T108 forward

<400> SEQUENCE: 1
catgtggaga taggtagaca ga                    22

<210> SEQ ID NO 2
<211> LENGTH: 21
<212> TYPE: DNA
<213> ORGANISM: artificial
<220> FEATURE:
<223> OTHER INFORMATION: primer T108 reverse

<400> SEQUENCE: 2
ccattctgag tagctgattc a                     21

```
<210> SEQ ID NO 3
<211> LENGTH: 20
<212> TYPE: DNA
<213> ORGANISM: artificial
<220> FEATURE:
<223> OTHER INFORMATION: primer T156 forward

<400> SEQUENCE: 3
tcttcctgac ctgtgtcttg                                              20

<210> SEQ ID NO 4
<211> LENGTH: 22
<212> TYPE: DNA
<213> ORGANISM: artificial
<220> FEATURE:
<223> OTHER INFORMATION: primer T156 reverse

<400> SEQUENCE: 4
gatgaatacc cagtcttgtc tg                                           22

<210> SEQ ID NO 5
<211> LENGTH: 20
<212> TYPE: DNA
<213> ORGANISM: artificial
<220> FEATURE:
<223> OTHER INFORMATION: primer T193 forward

<400> SEQUENCE: 5
agtccaagcc tgctaaataa                                              20

<210> SEQ ID NO 6
<211> LENGTH: 20
<212> TYPE: DNA
<213> ORGANISM: artificial
<220> FEATURE:
<223> OTHER INFORMATION: primer T193 reverse

<400> SEQUENCE: 6
ctgctgttgt catcattacc                                              20

<210> SEQ ID NO 7
<211> LENGTH: 22
<212> TYPE: DNA
<213> ORGANISM: artificial
<220> FEATURE:
<223> OTHER INFORMATION: primer T501 forward

<400> SEQUENCE: 7
ctcctcatta ttaccctgtg aa                                           22

<210> SEQ ID NO 8
<211> LENGTH: 19
<212> TYPE: DNA
<213> ORGANISM: artificial
<220> FEATURE:
<223> OTHER INFORMATION: primer T501 reverse

<400> SEQUENCE: 8
acatgctttg accaagacc                                               19

<210> SEQ ID NO 9
<211> LENGTH: 22
<212> TYPE: DNA
<213> ORGANISM: artificial
<220> FEATURE:
<223> OTHER INFORMATION: primer T115 forward

<400> SEQUENCE: 9
```
aatgtctgac tctaggtgag tg                                          22

<210> SEQ ID NO 10
<211> LENGTH: 20
<212> TYPE: DNA
<213> ORGANISM: artificial
<220> FEATURE:
<223> OTHER INFORMATION: primer T115 reverse

<400> SEQUENCE: 10
tttgctatct gagccactag                                             20

<210> SEQ ID NO 11
<211> LENGTH: 18
<212> TYPE: DNA
<213> ORGANISM: artificial
<220> FEATURE:
<223> OTHER INFORMATION: primer T107 forward

<400> SEQUENCE: 11
acatccgttc aggtgtga                                               18

<210> SEQ ID NO 12
<211> LENGTH: 22
<212> TYPE: DNA
<213> ORGANISM: artificial
<220> FEATURE:
<223> OTHER INFORMATION: primer T107 reverse

<400> SEQUENCE: 12
ccagaggtaa gataaatggt ga                                          22

<210> SEQ ID NO 13
<211> LENGTH: 19
<212> TYPE: DNA
<213> ORGANISM: artificial
<220> FEATURE:
<223> OTHER INFORMATION: primer T172 forward

<400> SEQUENCE: 13
agcatctccc ctttcaaca                                              19

<210> SEQ ID NO 14
<211> LENGTH: 19
<212> TYPE: DNA
<213> ORGANISM: artificial
<220> FEATURE:
<223> OTHER INFORMATION: primer T172 reverse

<400> SEQUENCE: 14
cttcccaacc caagtatcg                                              19

<210> SEQ ID NO 15
<211> LENGTH: 19
<212> TYPE: DNA
<213> ORGANISM: artificial
<220> FEATURE:
<223> OTHER INFORMATION: primer T507 forward

<400> SEQUENCE: 15
aggcagatgc ttcaccatc                                              19

<210> SEQ ID NO 16
<211> LENGTH: 19
<212> TYPE: DNA
<213> ORGANISM: artificial

```
<220> FEATURE:
<223> OTHER INFORMATION: primer T507 reverse

<400> SEQUENCE: 16
tgtggagcac ctcacacat                                            19

<210> SEQ ID NO 17
<211> LENGTH: 20
<212> TYPE: DNA
<213> ORGANISM: artificial
<220> FEATURE:
<223> OTHER INFORMATION: primer Haut14 forward

<400> SEQUENCE: 17
ccagggaaga tgaagtgacc                                           20

<210> SEQ ID NO 18
<211> LENGTH: 22
<212> TYPE: DNA
<213> ORGANISM: artificial
<220> FEATURE:
<223> OTHER INFORMATION: primer Haut14 reverse

<400> SEQUENCE: 18
tgaccttcac tcatgttatt aa                                        22

<210> SEQ ID NO 19
<211> LENGTH: 24
<212> TYPE: DNA
<213> ORGANISM: artificial
<220> FEATURE:
<223> OTHER INFORMATION: primer CSSM19 forward

<400> SEQUENCE: 19
ttgtcagcaa cttcttgtat cttt                                      24

<210> SEQ ID NO 20
<211> LENGTH: 24
<212> TYPE: DNA
<213> ORGANISM: artificial
<220> FEATURE:
<223> OTHER INFORMATION: primer CSSM19 reverse

<400> SEQUENCE: 20
tgttttaagc cacccaatta tttg                                      24

<210> SEQ ID NO 21
<211> LENGTH: 24
<212> TYPE: DNA
<213> ORGANISM: artificial
<220> FEATURE:
<223> OTHER INFORMATION: primer CSSM66 forward

<400> SEQUENCE: 21
aatttaatgc actgaggagc ttgg                                      24

<210> SEQ ID NO 22
<211> LENGTH: 25
<212> TYPE: DNA
<213> ORGANISM: artificial
<220> FEATURE:
<223> OTHER INFORMATION: primer CSSM66 reverse

<400> SEQUENCE: 22
acacaaatcc tttctgccag cttga                                     25
```